United States Patent [19]

Green

[11] 4,429,695

[45] Feb. 7, 1984

[54] SURGICAL INSTRUMENTS

[75] Inventor: David T. Green, Norwalk, Conn.

[73] Assignee: United States Surgical Corporation, Norwalk, Conn.

[21] Appl. No.: 394,132

[22] Filed: Jul. 1, 1982

Related U.S. Application Data

[63] Continuation of Ser. No. 118,664, Feb. 5, 1980, abandoned.

[51] Int. Cl.³ .................. A61B 17/04; A61B 17/11
[52] U.S. Cl. .................. 128/305; 128/334 R; 227/19; 227/76; 227/DIG. 1
[58] Field of Search .................. 128/334 R, 305, 321; 227/DIG. 1, 19, 135, 76; 30/124, 123, 289, 286

[56] References Cited

U.S. PATENT DOCUMENTS

| | | |
|---|---|---|
| 3,078,465 | 2/1963 | Bobrov . |
| 3,079,606 | 3/1963 | Bobrov et al. . |
| 3,080,564 | 3/1963 | Strekopitov et al. . |
| 3,252,643 | 5/1966 | Strekopytov et al. . |
| 3,275,211 | 9/1966 | Hirsch et al. . |
| 3,315,863 | 4/1967 | O'Dea . |
| 3,317,105 | 5/1967 | Astafjev et al. . |
| 3,490,675 | 1/1970 | Green et al. . |
| 3,494,533 | 2/1970 | Green et al. . |
| 3,499,591 | 3/1970 | Green . |
| 4,060,089 | 11/1977 | Noiles . |
| 4,241,861 | 12/1980 | Fleischer . |

FOREIGN PATENT DOCUMENTS

| | | |
|---|---|---|
| 869527 | 3/1953 | Fed. Rep. of Germany . |
| 7909218 | 5/1979 | Fed. Rep. of Germany . |
| 1278616 | 9/1959 | France . |
| 2310117 | 12/1976 | France . |
| 375481 | 4/1964 | Switzerland . |
| 1158111 | 7/1966 | United Kingdom . |
| 1158113 | 7/1966 | United Kingdom . |

Primary Examiner—Michael H. Thaler

[57] ABSTRACT

A surgical stapling instrument has upper and lower elongate jaws for receiving a staple cartridge and an anvil respectively. A pusher bar and knife assembly including a pair of pusher bars and a central knife carrier moves longitudinally relative to the jaws to eject staples sequentially from the magazine and to form laterally spaced staple rows in tissue gripped between the jaws while the knife cuts the tissue along a line between the staple rows. The instrument includes structure for locally supporting the jaws in the region of the pusher bar cams and knife blade as these elements move along the jaws to resist forces created during staple ejection and shaping which tend to vertically separate and/or laterally distort the jaws.

19 Claims, 14 Drawing Figures

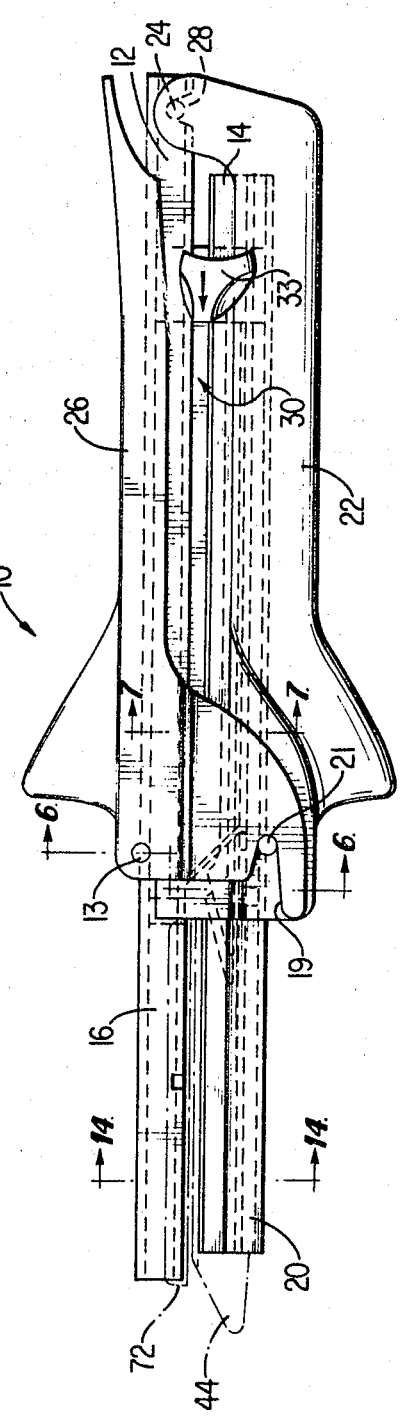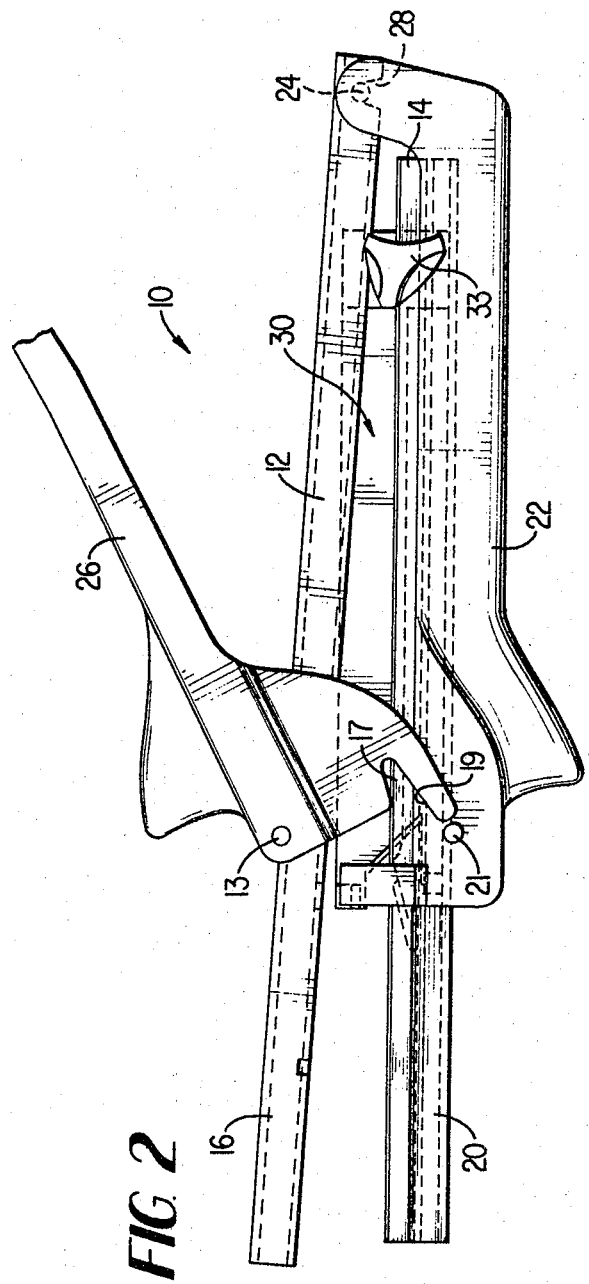

SURGICAL INSTRUMENTS

This is a continuation, of application Ser. No. 118,664, filed Feb. 5, 1980, now abandoned.

BACKGROUND OF THE INVENTION

This invention relates to an instrument for use in applying surgical fasteners such as staples, clips and the like to living tissue. More particularly, the invention relates to a surgical stapling instrument for use in forming a plurality of laterally spaced rows of staples in an internal body organ. Typically, such an instrument comprises a pair of cooperating elongate jaw members, one of which in use carries a staple cartridge with at least two laterally spaced rows of staples and the other of which carries an anvil with staple-closing depressions aligned with the rows of staples in the cartridge. A pusher bar and knife assembly is provided which is moved longitudinally along the jaws to sequentially eject staples from the cartridge by a camming action, through the agency of staple pushers carried by the cartridge in association with the individual staples, and to close the staples against the anvil, thereby forming laterally spaced lines of staples in tissue gripped between the jaws, while the knife, which trails the pusher bars, cuts the tissue along a line between the staple rows. One instrument of this type is disclosed for example in U.S. Pat. No. 3,499,591, commonly assigned herewith and the disclosure of which is incorporated herein by reference.

With instruments of the above type, the staple cartridges and associated anvils, pusher bars and knife assemblies have commonly been made of disposable plastics and low cost metal stampings while the frames, namely the basic instruments have more generally been constructed for repeated usage, necessitating continual sterilization of these elements before each reuse. In recent years, in order to obviate the need for such repeated sterilization of instruments, the tendency in the surgical field has been towards the introduction of fully self-contained disposable instruments which are used for only a single operation and then discarded. Obviously, therefore, in the design of such disposable instruments, economics is a factor, and it is desirable to design such instruments to utilize readily available economic materials of minimum material weight and to employ production techniques of optimum economy.

With stapling instruments of the type described, relatively large forces are involved in clamping the tissue to be fastened and in ejecting the individual staples, causing these to penetrate the gripped tissue and to be closed against the anvil. Such forces tend both to separate the jaws vertically and to laterally distort the jaws, thereby hindering accurate stapling. This problem is of course accentuated if relatively light-weight disposable materials are to be used for manufacture of the jaw frames.

It is an object of the present invention to provide an instrument of the character described for applying surgical fasteners, in which optimum alignment and stabilization of the jaws is obtained during application and securing of the fasteners.

Another object of the invention is to provide a novel form of instrument for use in applying surgical fasteners to living tissue and which is particularly suited to use in surgical stapling procedures.

It is a further object of the invention to provide a surgical stapling or like fastening instrument having a design which allows the instrument to be manufactured in the main from relatively light weight disposable materials while still providing proper alignment and stabilization of the jaws during stapling.

SUMMARY OF THE INVENTION

In accordance with the invention, the elongate jaws of a surgical stapling instrument of the kind described are locally supported during stapling, substantially at the point where maximum jaw deflecting forces occur, by support means which move along the jaws with the pusher bar and knife assembly. To provide for lateral alignment and vertical stabilization of the jaws during stapling, each jaw is formed with a longitudinal channel or passageway and the pusher bar and knife assembly carries upper and lower support shoes which are accurately laterally aligned with one another and which fit closely in the respective passageways when the jaws are closed, so that the shoes travel along the passageways when the pusher bar and knife blade assembly is operated.

The shoes are located on the pusher bar and knife blade assembly in the region of the pusher bar cams and the knife blade and their effect is to provide localized support for the jaws in the region of these elements as they progress along the jaws, thereby providing proper jaw alignment in the region of the individual staples as these are sequentially acted upon by the pusher bars. Further, the shoes are not only laterally but also vertically confined in the passageways and thereby serve to resist vertical jaw-opening forces during staple formation.

Conveniently, the jaw passageways are formed towards the outside of the respective jaws and the shoes are carried on upper and lower extensions of the knife carrier, which is made of relatively rigid material affording adequate lateral support to the shoes and hence to the jaws at the point of stapling as the shoes move therealong. To allow passage of the vertically extended knife carrier along the jaws, the staple cartridge and the anvil which are supported on the inner facing surfaces of the respective jaws are each composed of two laterally spaced elongate members carried by the respective jaws so that the extended knife carrier can move through spaces formed between the respective elongate members.

By utilizing the aforementioned shoes locally to support the jaws and provide both lateral and vertical stabilization in the region of the pusher bar cams and knife blade as these elements ride along the jaws, the adverse effects of the previously mentioned forces are substantially minimized and the jaws themselves can therefore be made of light-weight construction so that an instrument designed in accordance with the invention lends itself to manufacture in disposable materials.

BRIEF DESCRIPTION OF DRAWINGS

FIG. 1 is a side view of a surgical stapling instrument in the assembled and closed condition;

FIG. 2 is a side view of the instrument in an open condition;

DESCRIPTION OF THE PREFERRED EMBODIMENT

Figure 3:
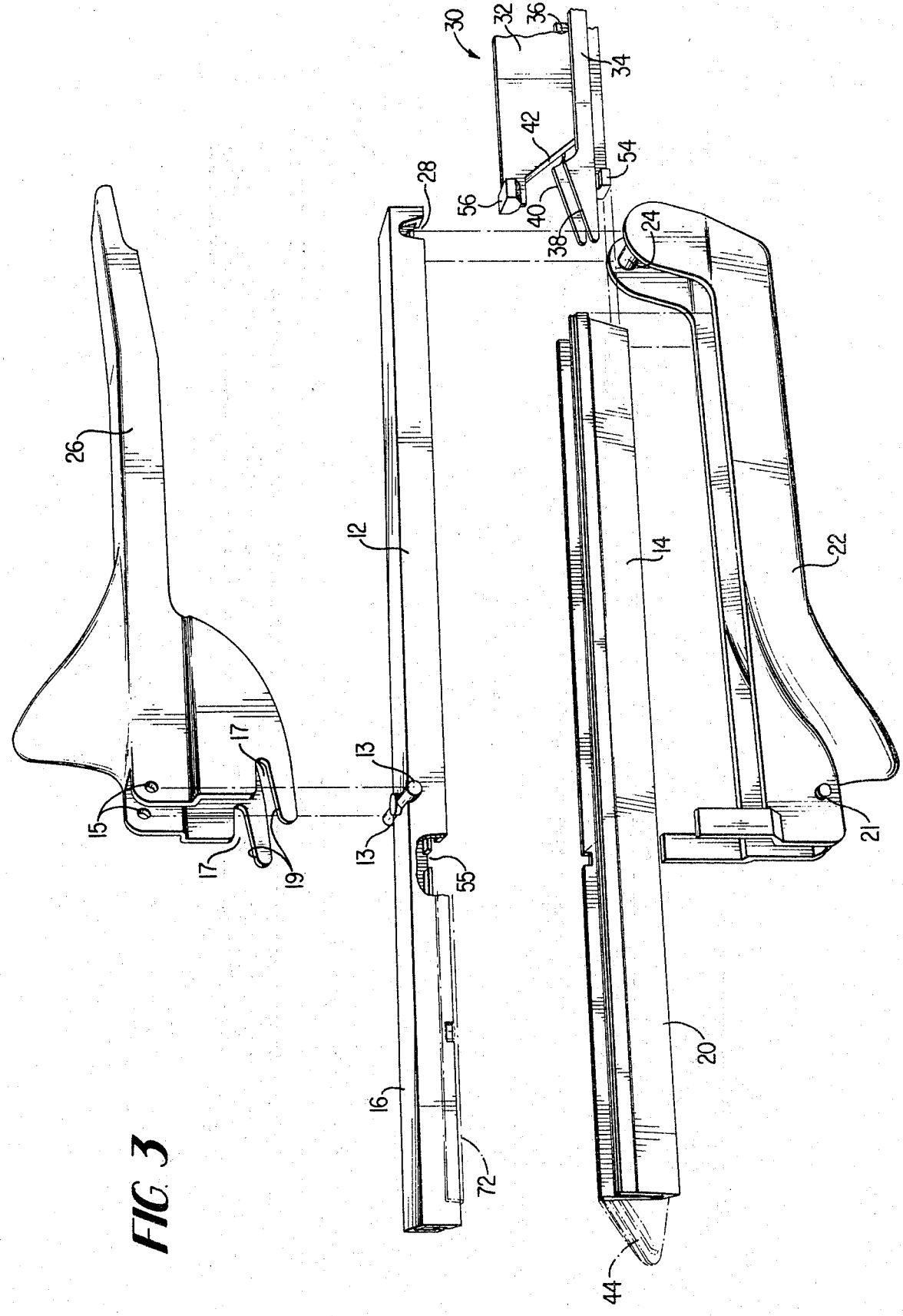
FIG. 3 is an exploded view of the instrument.

It is to be noted that the general construction and principle of operation of the illustrated instrument is similar to the instrument described in U.S. Pat. No. 3,499,591 previously referred to. Accordingly, the following description will only deal in detail with modified features of the instrument and for a fuller understanding of the principles and operation of the instrument, reference may be made to the above patent, the disclosure of which is incorporated herein by reference.

The present instrument, generally indicated by reference 10 includes an upper frame 12 and a lower frame 14. The forward end portion of upper frame 12 defines an elongate upper jaw 16 while the forward end portion of the lower frame 14 defines an elongate lower jaw 20. The portion of lower frame 14 rearward of jaw 20 fits into a channel-shaped handle member 22 having a pivot bar 24 at its rear end which is received in notches 28 at the rear end of upper frame member 12. Intermediate its length, upper frame member 12 has laterally projecting lugs 13 which fit in complementary openings 15 formed in a bifurcated locking handle 26. The handle 26 can be used to open and close the frames about the pivot means 24, 28 between the open condition shown in FIG. 2 and the locked condition shown in FIG. 1. To this end, handle 26 has slots 17 providing camming surfaces 19 which cooperate with laterally projecting lugs 21 on handle member 22. The instrument further includes a sliding pusher bar and knife assembly 30 comprising a central knife carrier 32 and laterally spaced pusher bars 34 and 36 on either side the knife carrier, the pusher bars terminating at their forward ends in inclined pusher bar cams 38 and 40, respectively, and the knife carrier including an inclined knife 42 situated just to the rear of the pusher bar cams.

In use, a disposable staple cartridge 44, containing four laterally spaced longitudinal rows of staples, is inserted into the lower jaw 20 while two anvil members 72 having staple shaping depressions in their outer surfaces, complimentary to the positioning of the individual staples in the staple cartridge, are placed on the upper jaw 16. The instrument is inserted into a patient's body and manipulated such that tissue to be cut and sutured is inserted between the jaws, an incision to receive one of the jaws having previously been made in the tissue, if required. The jaws are then closed and locked by handle 26 to firmly grip the tissue between the opposing staple cartridge and anvil surfaces. The pusher bar and knife assembly, which is initially in a rearward position relative to the jaws, is then pushed forward causing the pusher bar cams to enter longitudinal slits in the staple cartridge, in which slits are accommodated rows of individual staple pushers. The pusher bar cams cooperate sequentially with camming surfaces on the individual staple pushers to force the staples successively from the cartridge, through the gripped tissue and into engagement with the anvil depressions which thereby, in conjunction with the cams, produce staple-closing forces. The design of the cartridge is such that each slit carries two mutually staggered rows of staples so that in all, four staple rows are formed in the gripped tissue. The knife 42, which trails the pusher bar cams slightly and rides in central longitudinal slits in the cartridge and anvil, cuts the gripped tissue along a line between the two pairs of staple rows.

To provide lateral support for the jaws and to resist forces tending to vertically open the jaws during stapling, each jaw is provided with a longitudinal passageway and the knife blade carrier 32, which is a relatively rigid member, preferably of metal, carries upper and lower laterally aligned shoes 56 and 54, respectively, which ride in these passageways and provide the required local support to the jaws in the region of the pusher bar cams and knife blade as these elements travel along the staple cartridge.

Figure 6:
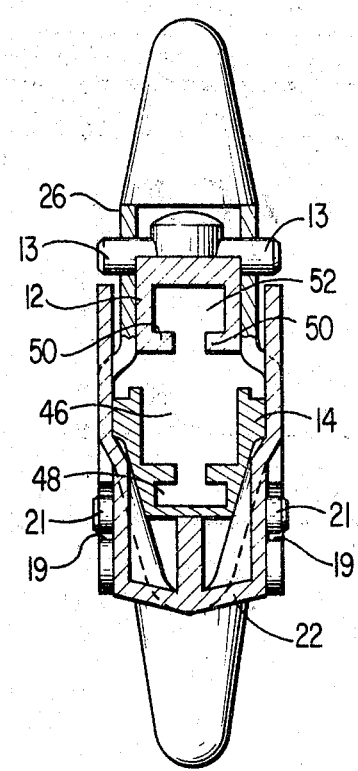
FIG. 6 is a section on line 6—6 of FIG. 1.
Figure 7:
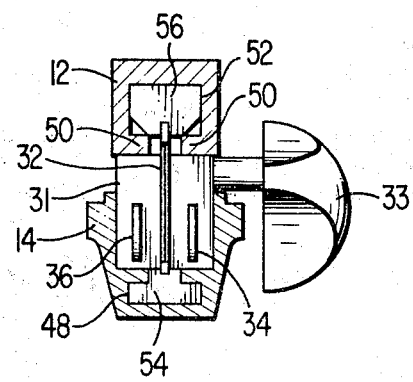
FIG. 7 is a section on line 7—7 of FIG. 1, with parts of the instrument removed.
Figure 14:
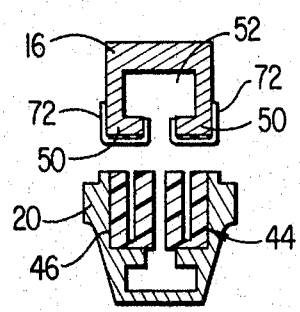
FIG. 14 is a section on line 14—14 of FIG. 1.

Thus, it will be seen, particularly in FIGS. 6, 7 and 14, that the lower frame 14 is formed with a cartridge-receiving channel 46 and an outer longitudinal passageway 48 of generally T-shaped cross-section extending from the base of the channel 46. Upper frame 12 has inwardly directed longitudinally extending shoulders 50 for mounting the anvils as will be described, the construction of the upper frame being such that a longitudinally extending passageway 52 of generally rectangular section is formed beneath the shoulders.

Figure 4:
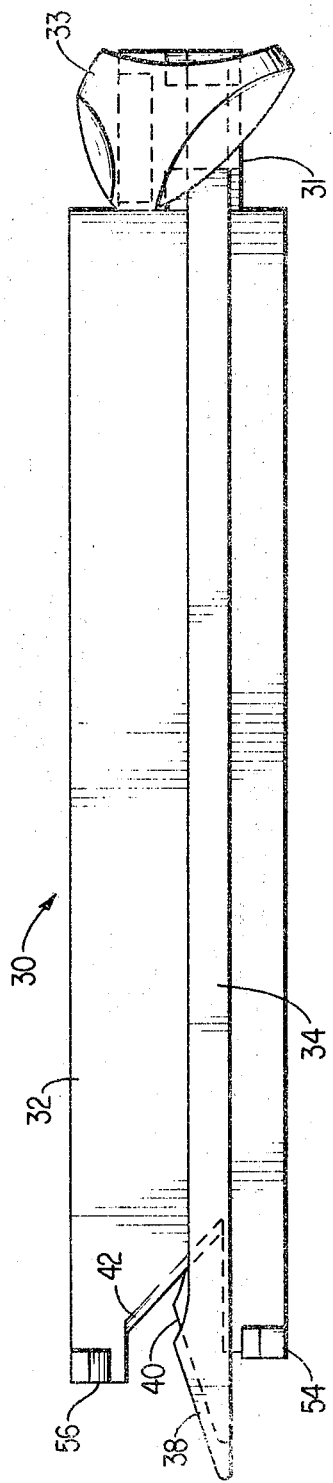
FIG. 4 is a side view of a pusher bar and knife assembly.
Figure 5:
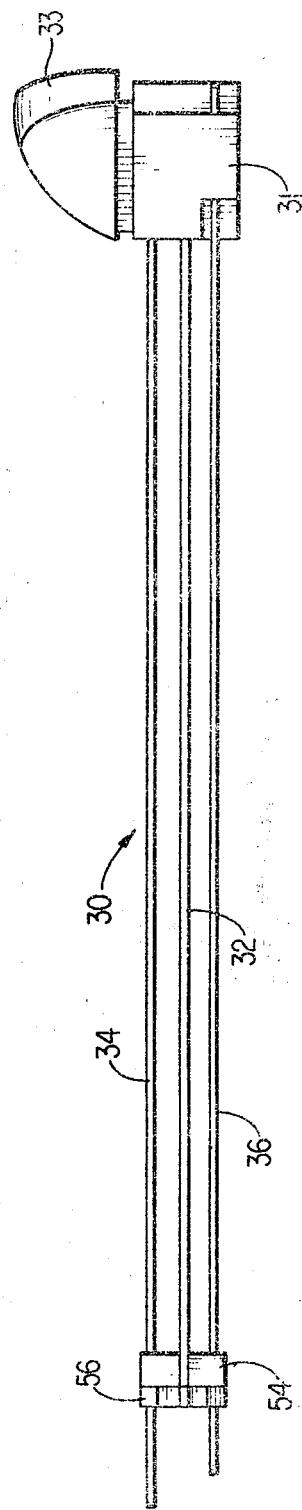
FIG. 5 is an underneath plan view of the pusher bar and knife assembly.

The pusher bar and knife assembly 30, see particularly FIGS. 3, 4 and 5, has conventional-type laterally spaced pusher bars 34 and 36 terminating in slightly offset inclined pusher bar cams 38 and 40. The central knife carrier 32, as indicated, has an inclined knife 42 just to the rear of the pusher bar cams and the knife carrier is extended vertically above and below the pusher bars. On upper and lower terminal portions of the knife carrier which project forward of the knife are situated lower and upper shoes 54 and 56, respectively, the vertical spacing between the shoes corresponding to the vertical spacing between the passageways 48 and 52 in the lower and upper frames when the frames are locked together. The lower shoe 54 has a substantially T-shaped cross section corresponding to the cross-sectional shape of passageway 48 so that this shoe fits in passageway 48 with minimal clearance to allow substantially friction-free passage of the shoe along the passageway, and upper shoe 56 is likewise shaped to fit in passageway 52 with minimal clearance to provide substantially friction-free passage. It will be noted that the shoes 52 and 54 are longitudinally located in proximity to the pusher bar cams 38 and 40 so as to provide support in use for the jaws 16 and 20 in the region of the cams substantially at points where the forces created by cooperation of the pusher bar cams and the individual staple pushers in the cartridge approach a maximum. Further, by locating the shoes both laterally and vertically in the respective passageways, both lateral alignment of the jaws and resistance to vertical jaw opening during stapling is obtained.

At the rear end of assembly 30, the pusher bars and knife carrier are mounted in known manner in a suitable carrying block 31 having an operating knob 33 or the like.

Figure 8:
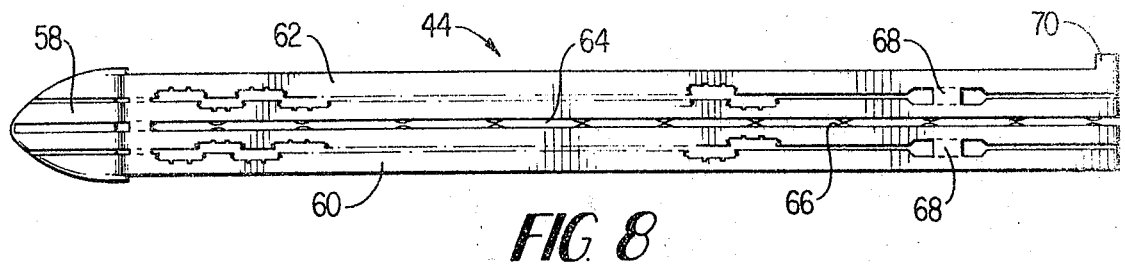
FIG. 8 is an underneath view of a disposable staple cartridge.
Figure 9:
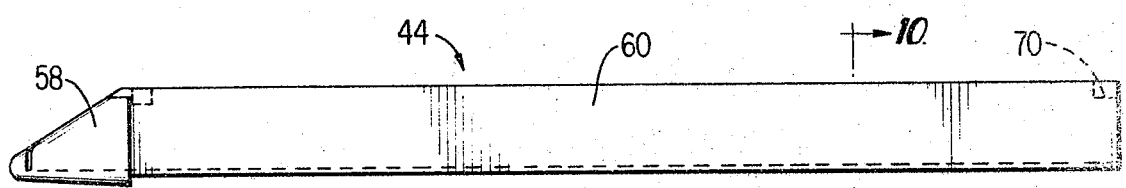
FIG. 9 is a side view of the cartridge.
Figure 10:
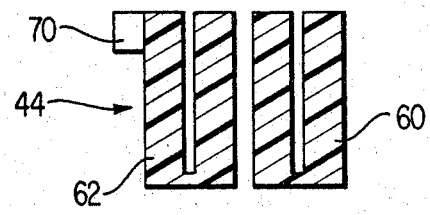
FIG. 10 is a section on line 10—10 of FIG. 9.

The staple cartridge 44 as shown in FIGS. 8, 9 and 10 is generally of similar character to the known type as described in the aforementioned U.S. Pat. No. 3,499,591 insofar as the number of staple rows, and design and location of the individual staple pushers are concerned. For a fuller description of these elements and the manner in which staple ejection is effected by interaction of the pusher bar cams and the individual staple pushers, reference may therefore be made to that patent. In the present case, the cartridge 44 has a solid nose portion 58 and a pair of longitudinal ribs 60 and 62 extending rearward from the nose portion and defining a slit 64 therebetween right through the cartridge for passage of the knife carrier 32. The inner facing surfaces of the ribs 60 and 62 have bumps 66 to laterally locate the knife carrier, and the ribs are themselves longitudinally slit to accommodate the staple pushers and the opposed, staggered rows of staples. Friction pieces 68 are provided to inhibit inadvertent forward motion of the pusher bars. Thus, the significant difference between the present cartridge and that described in U.S. Pat. No. 3,499,591 is that in the present case slit 64 extends right through the cartridge (to the rear of the nose portion) to allow passage of the vertically extended knife carrier. In use, as indicated, the cartridge 44 sits in the cartridge receiving channel 46 of the upper jaw with the nose portion 58 projecting forward of the jaw, positive longitudinal location of the cartridge being effected by means of a projecting cartridge lug 70 and a complementary cutout in one of the side walls of channel 46.

While the instrument has been herein described as utilizing a separate staple cartridge 44 in like manner to the instrument described in U.S. Pat. No. 3,499,591, it is contemplated within the scope of the present invention for the staple cartridge to be formed as an integral part of lower jaw 20.

Figure 11:
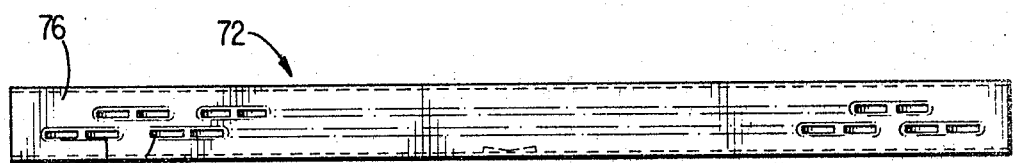
FIG. 11 is a top view of an elongate anvil member.
Figure 12:
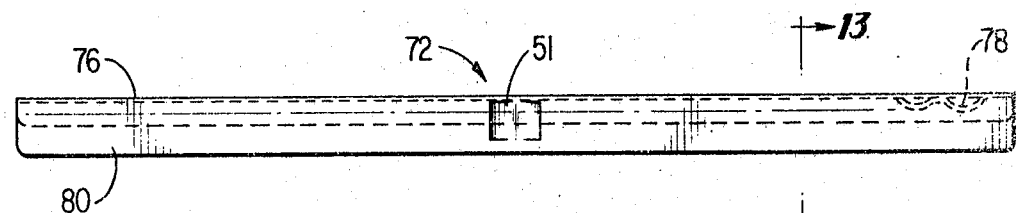
FIG. 12 is a side view of the anvil member.
Figure 13:
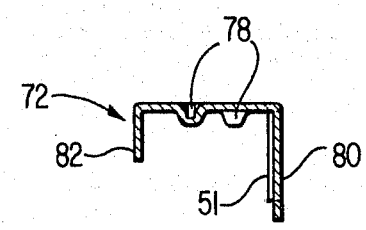
FIG. 13 is a section on line 13—13 of FIG. 12.

The anvil means in the present instance, see FIGS. 11, 12 and 13, comprises a pair of like individual elongate anvils 72 which sit with a friction fit on the shoulders 50 of the upper jaw, as seen in FIGS. 1, 3 and 14, whereby a slit is provided between the anvils allowing passage for the vertically extended knife carrier. Each individual anvil comprises an anvil surface 76 with staple-shaping depressions 78, an outer wall 80 and a shorter inner wall 82. The inner and outer walls are slightly inwardly tapered to provide the friction fit on shoulders 50 and the outer walls each have depressions 51 aligning with complimentary depressions in the side walls of the lower jaw for longitudinally locating the individual anvils and accurately aligning the staple shaping depressions with the individual staples in cartridge 44.

While the instrument as described includes separate anvils 72 which fit on the shoulders 50 of upper jaw 16, it is also possible, particularly in the manufacture of a low-cost disposable instrument, to dispense with the anvils themselves and form the staple shaping depressions directly in the undersurfaces of shoulders 50 of the upper jaw.

Assembly of the various components of the instrument is effected in the following manner with particular reference to FIGS. 1 to 3. Initially, with a cartridge 44 correctly positioned on jaw 20 of lower frame 14, the forward end of pusher assembly 30 is inserted from the back into lower frame 14, with lower shoe 54 fitting in passageway 48, and assembly 30 is moved forward along frame 14 until the pusher bars enter the longitudinally slit ribs 60 and 62 of cartridge 44 and are arrested by the friction pieces 68. This position of pusher assembly 30 relative to frame 14 is shown in FIGS. 1 and 2. Frame 14 with the inserted pusher assembly 30 is then fitted into handle member 22, suitable complementary locating means (not shown) being provided on the frame and handle member to longitudinally align these elements and prevent forward movement of frame 14 in member 22 during staple ejection.

Anvils 72 are fitted on jaw 16, and lugs 13 of frame 12 are fitted into openings 15 of handle 26. Then with handle 26 tilted upwardly, as shown in FIG. 2, notches 28 are engaged with pivot bar 24 to complete the assembly of the instrument.

In use, the instrument in the assembled open condition, substantially as shown in FIG. 2, is inserted into a body cavity, so that tissue to be stapled is accepted between jaws 16 and 20, and the instrument is then locked by manipulation of handle 26 and cooperation of camming surfaces 19 with lugs 21. It will be noted that openings 55 (see FIG. 3) are provided in shoulders 50 of the upper frame 12 which allow shoes 56 to enter channel 52 as the instrument is closed. With tissue gripped between the jaws and the instrument in the condition shown in FIG. 1, stapling is effected in the manner described in the aforementioned patent by pushing forward on knob 33.

When stapling is completed, the pusher assembly 30 is retracted to the initial position, allowing shoes 56 to be removed from channel 52 through openings 55, so that the instrument can be opened.

It will be appreciated, since the shoes 54 and 56 are accurately laterally aligned and carried by a relatively rigid member, that during stapling, as the shoes move along the passageways 48 and 52 with minimal clearance, they provide adequate localized support to the jaws in the region of operation of the pusher bar cams and the particular individual staple pushers being actuated. Due to the cross-sectional shape of the shoes and passageways, such support resists forces tending both laterally to distort the jaws and to open the jaws vertically, and accordingly the present construction lends itself to manufacturing the jaws in relatively light weight disposable materials. It is to be understood, however, that the construction can also be used in instruments manufactured from more conventional materials.

While only a single preferred embodiment of the invention has been described in detail, it is to be understood that the invention is not limited to its specific features and modifications are possible within the scope of the attached claims. Thus, while the invention has been particularly described in relation to its application in a surgical stapling instrument, the invention is not limited to this application. The invention may be applied to other fastening instruments having opposed jaws which require stabilization while fastening means are applied to living tissue gripped between the jaws. For example, the invention may be applied to instruments for applying certain types of surgical clips or instruments for applying surgical fastening devices of the type set out in U.S. Pat. No. 4,060,089.

What is claimed is:

1. In a surgical stapling instrument having first and second cooperating frames each provided with an elongate jaw, one of said jaws being adapted to receive at least two laterally spaced longitudinal rows of staples, an elongate pusher bar and knife assembly slidable longitudinally relative to said jaws for sequentially ejecting staples from said one of said jaws and shaping the staples against anvil means provided on the other of said jaws to form a pair of laterally spaced staple rows in tissue gripped between said jaws and for cutting the tissue along a line between said staple rows, said assembly including a pair of laterally spaced pusher bars each having a foward end portion including a pusher bar cam and a knife carrier having a knife blade located between said pusher bars, the improvement comprising jaw support means carried by said pusher bar and knife assembly and cooperating with said jaws for locally supporting both of said jaws in the region of said pusher bar cams as said cams move along said jaws for resisting forces tending to deflect said jaws during ejection and shaping of the individual staples.

2. The improvement of claim 1 wherein said support means includes means for resisting forces tending to laterally distort said jaws.

3. The improvement of claim 1 wherein said support means includes means for resisting forces tending to vertically separate said jaws.

4. The improvement of claim 1 wherein said support means includes means for resisting forces tending to laterally distort said jaws and forces tending to vertically separate said jaws.

5. The improvement of claim 1 wherein each of said jaws has a longitudinal passageway defined therein and wherein said support means includes upper and lower shoes carried by said pusher bar and knife assembly in the region of said pusher bar cams, said shoes fitting in said passageways and travelling therealong during longitudinal movement of said assembly to provide said local support for said jaws.

6. The improvement of claim 5 wherein said passageways and shoes have complementary cross-sectional shapes resisting localized lateral misalignment of the jaws and resisting vertical separation of the jaws.

7. The improvement of claim 6 wherein at least one of said shoes and the corresponding jaw passageway have complementary substantially T-shaped cross-sectional profiles.

8. The improvement of claim 5 wherein said knife carrier includes upper and lower portions projecting forwardly of said knife and wherein said shoes are disposed on the projecting portions above and below the level of said pusher bar cams, respectively.

9. The improvement of claim 1 wherein said jaws are made of light-weight disposable plastics material and said knife carrier is made of relatively rigid material, whereby said shoes provide support to said jaws resisting said jaw deflecting forces.

10. The improvement of claim 1 including a staple cartridge for mounting on said one of said jaws to provide said rows of staples, said cartridge comprising a pair of longitudinally extending staple-carrying elements defining a slit therebetween for passage of said knife carrier when said cartridge is mounted on said one of said jaws.

11. The improvement of claim 10 wherein said cartridge has a common nose portion and said staple-carrying elements each extend rearward from said nose portion.

12. The improvement of claim 1 including anvil means comprising a pair of elongate anvil members and means for mounting said anvil members on the other of said jaws to define a slit therebetween for passage of said knife carrier.

13. The improvement of claim 12 wherein each of said anvil members is substantially channel-shaped in cross section and said other of said jaws includes opposed inwardly directed longitudinal shoulders defining said anvil mounting means, said anvil members seating on said shoulders with a friction fit.

14. The improvement of claim 1 including means for pivotally connecting said frames together at the rear ends of said frames and a locking handle means pivotally connected to one of said frames and cooperating with locking formations associated with the other of said frames for moving said jaws between open and closed conditions.

15. The improvement of claim 1, wherein said jaw support means is disposed at least partially between said jaws.

16. A surgical instrument for use in fastening living tissue comprising upper and lower cooperating elongated jaws movable between open and closed positions, whereby tissue to be fastened may be gripped between said jaws when said jaws are in the closed position, means associated with one of said jaws for mounting a tissue fastening means, a pusher means movable longitudinally relative to said jaws when said jaws are in said closed position for forcibly expelling said fastening means from said one jaw and causing said fastening means to penetrate tissue gripped between said jaws, and jaw support means carried by said pusher means, said jaw support means cooperating with said jaws during movement of said pusher means along said jaws for resisting forces tending to separate said jaws during expulsion of said fastening means.

17. A surgical instrument as defined in claim 16 wherein said jaw support means includes means for resisting forces tending to laterally operate said jaws during expulsion of said fastening means.

18. A surgical instrument as defined in claim 16 or claim 17 wherein said jaw support means includes means for resisting forces tending to vertically separate said jaws during expulsion of said fastening means.

19. A surgical instrument as defined in claim 16 wherein said jaw support means includes upper and lower support shoes carried by said pusher means and wherein each of said jaws includes a longitudinal passageway for receiving respective one of said shoes, said shoes travelling in said passageways during movement of said pusher means along said jaws and locally supporting said jaws in the region of said respective shoes.

* * * * *